United States Patent [19]

Hirai et al.

[11] Patent Number: 4,637,902

[45] Date of Patent: Jan. 20, 1987

[54] MIXED ANHYDRIDES OF CARBAMIC AND HYDROXAMIC ACIDS

[75] Inventors: Hiroyuki Hirai; Ken Kawata, both of Kanagawa, Japan

[73] Assignee: Fuji Photo Film Co., Ltd., Kanagawa, Japan

[21] Appl. No.: 589,289

[22] Filed: Mar. 14, 1984

[30] Foreign Application Priority Data

Mar. 14, 1983 [JP] Japan ................................ 58-42673

[51] Int. Cl.$^4$ .................... C07C 83/10; C07C 125/00

[52] U.S. Cl. ................................ 260/545 R; 544/162; 544/335; 544/388; 546/312; 546/329; 548/196; 548/558; 548/567; 549/71; 549/486; 558/393; 558/401; 558/413; 558/417; 562/442; 562/565; 430/179; 430/617

[58] Field of Search .................... 260/545 R; 544/162, 544/335, 388; 546/312, 329; 548/196, 558, 567; 549/71, 486; 558/393, 401, 413, 417; 562/442, 565

[56] References Cited

FOREIGN PATENT DOCUMENTS 1267208 5/1968 Fed. Rep. of Germany ... 260/545 R

OTHER PUBLICATIONS

Zoerkendoerfer, E. *Z. Naturforsch. B. Anorg. Chem. Org. Chem.*, (1977), 32B(11), 1304–7.

*Primary Examiner*—Natalie Trousof
*Assistant Examiner*—L. Hendriksen
*Attorney, Agent, or Firm*—Sughrue, Mion, Zinn, Macpeak and Seas

[57] ABSTRACT

A base precursor represented by the following general formula (A) or (B):

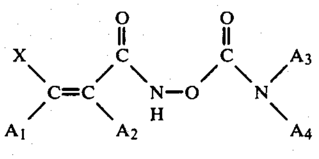

(A)

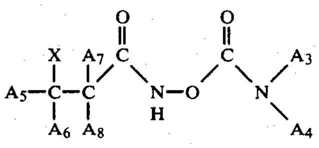

(B)

wherein $A_1$, $A_2$, $A_5$, $A_6$, $A_7$, and $A_8$ each represents a hydrogen atom, an alkyl group, a substituted alkyl group, a cycloalkyl group, an alkenyl group, an aralkyl group, an aryl group, a substituted aryl group, an acyl group, or a heterocyclic group, and $A_1$ and $A_2$ can combine to form a ring and two of $A_5$, $A_6$, $A_7$, and $A_8$ can combine to form a ring, $A_3$ and $A_4$ each represents a hydrogen atom, an alkyl group, a substituted alkyl group, a cycloalkyl group, or an aralkyl group, and $A_3$ and $A_4$ can combine to form a ring or $A_3$ and $A_4$ can be a double bond forming an imino group from

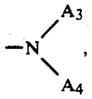

, and X represents a nucleophilic group.

5 Claims, No Drawings

MIXED ANHYDRIDES OF CARBAMIC AND HYDROXAMIC ACIDS

FIELD OF THE INVENTION

This invention relates to novel base precursors which release a basic component by thermal decomposition.

BACKGROUND OF THE INVENTION

Stability is of importance, with base precursors which can be put into practical use. Hence, great importance is attached to those base precursors which are stable and neutral at ordinary temperatures and which release a base only when heated. For example, stable compounds like urea are being used as described in U.S. Pat. No. 2,732,299, Belgian Pat. No. 625,554, etc.

Further, a technique of using urea of the ammonium salt of a weak acid (Japanese Pat. Publication No. 1699/65), a technique of using hexamethylenetetramine or semicarbazide (U.S. Pat. No. 3,157,503), a technique of using alkylamines, allylamines, etc. (Japanese Pat. Publication No. 8141/65), and the like, are known.

In addition, a technique of using hydrophobic guanidine derivatives (Japanese Patent Application (OPI) No. 45094/82) (The term "OPI" as used herein refers to a "published unexamined Japanese Patent Application") and a technique of using triazine compounds and carboxylic acids (U.S. Pat. No. 3,493,374) are also known.

Japanese Pat. Publication No. 18704/64 describes a technique of coating an acidic substance on soluble base particles, West German Pat. No. 119,516 describes a technique of encapsulating with wax, Japanese Pat. Publication No. 34792/64 and U.S. Pat. No. 3,284,201 describe a technique of forming a protective layer or an interlayer of a high molecular weight substance, Japanese Pat. Publication Nos. 2145/66, 2146/66, and 15466/66 describe a technique of forming a light-sensitive layer by dispersing in a binder using an organic solvent, and U.S. Pat. Nos. 3,653,091, 3,255,011, 3,294,534, 3,298,834 and 3,301,679, and French Pat. No. 1,405,427 describe a technique of using thermally decomposable acids.

Although various techniques as described above have been proposed, excellent techniques have not yet been attained. Because, light-sensitive materials using this type of compound capable of producing a base upon heating have poor preservability and fail to produce sufficient base upon being heated, thus failing to provide high image density. Further, thermal decomposition products such as colored products (e.g., tar) and white crystals are produced.

SUMMARY OF THE INVENTION

An object of the present invention is to provide novel compounds which remove the defects present in conventional base precursors, that is, to provide novel base precursors which are stable at ordinary temperature and, when heated to temperatures higher than a certain temperature, rapidly release a basic substance.

The above-described object of the present invention has been attained by the base precursors represented by the following general formula (A) or (B):

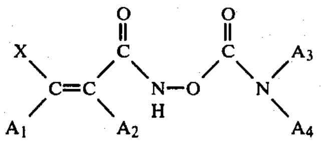
(A)

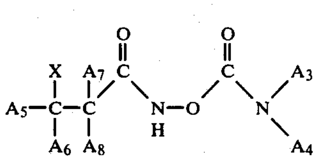
(B)

wherein $A_1$, $A_2$, $A_5$, $A_6$, $A_7$, and $A_8$ each represents a hydrogen atom, an alkyl group, a substituted alkyl group, a cycloalkyl group, an alkenyl group, an aralkyl group, an aryl group, a substituted aryl group, an acyl group or a heterocyclic group, and $A_1$ and $A_2$ can combine to form a 5- or 6-membered aromatic ring or a 5- or 6-membered heterocyclic group containing an oxygen atom, a sulfur atom or a nitrogen atom and, further, two of $A_5$, $A_6$, $A_7$, and $A_8$ can combine to form a ring, e.g., a cycloaliphatic ring such as a cyclohexyl group, etc., $A_3$ and $A_4$ each represents a hydrogen atom, an alkyl group, a substituted alkyl group, a cycloalkyl group or an aralkyl group, and $A_3$ and $A_4$ can combine to form a ring or $A_3$ and $A_4$ can be a double bond forming an imino group from

, and X represents a nucleophilic group.

DETAILED DESCRIPTION OF THE INVENTION

Examples of alkyl groups for the compounds of this invention include a straight or branched chain alkyl group containing 1 to 18 carbon atoms, e.g., a methyl group, etc., and examples of substituents for the substituted alkyl groups for $A_1$ to $A_8$ include a hydroxy group, an alkoxy group, a cyano group, a carboxyl group, a carboalkoxy group, a carbamoyl group, a halogen atom, (e.g., chlorine, etc.) etc.

Examples of cycloalkyl groups include 5- to 6-membered cycloalkyl groups containing 5 to 10 carbon atoms, e.g., a cyclohexyl group, etc., and examples of alkenyl groups include an alkenyl group containing 2 to 10 carbon atoms, e.g., an allyl group, a crotyl group, a cinnamyl group, a vinyl group, etc.

Examples of aralkyl groups include an aralkyl group containing 7 to 10 carbon atoms, e.g., a benzyl group, a β-phenethyl group, a benzhydryl group, etc., examples of aryl groups include a monocyclic or bicyclic group containing 5 to 15 carbon atoms, e.g., a phenyl group, a naphthyl group, an anthryl group, etc., and examples of substituents for the substituted aryl groups include an alkyl group, an alkoxy group, a dialkylamino group, a cyano group, a nitro group, a halogen atom, etc. Examples of heterocyclic groups include 5 to 7 membered group containing one or more of a N atom, a S atom and a O atom as hetero atoms, e.g., a pyridyl group, a furyl group, a thienyl group, a pyrrole group, an indolyl group, etc., and examples of acyl groups include acyl groups containing 2 to 18 carbon atoms which are derived from aliphatic or aromatic carboxylic acids, e.g., an acetyl group, etc. Examples of rings formed when $A_3$ and $A_4$ combine to form a ring include

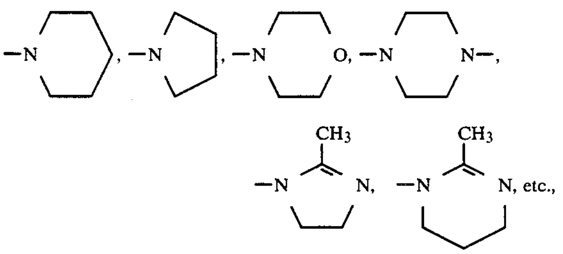

and examples where the group

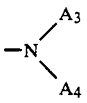

represents an imino group include

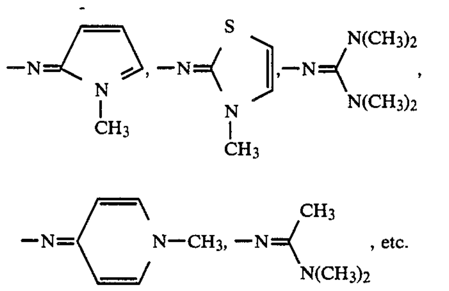

Suitable nucleophilic groups represented by X are, for example, a hydroxy group, a hydroxymethyl group, an amino group, a substituted amino group, an aminomethyl group, a substituted aminomethyl group, a mercapto group, a mercaptomethyl group, a carboxyl group, a carbamoyl group, a substituted carbamoyl group, a sulfamoyl group, a substituted sulfamoyl group, etc.

Of the base precursors represented by the above general formulae, compounds of general formula (A) are preferred, with compounds of general formula (A) wherein $A_1$ and $A_2$ form an aromatic or heterocyclic ring being more preferred. Particularly, the most preferred compounds are represented by following general formula (C):

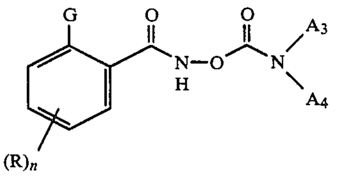

(C)

wherein G represents a nuclophilic group, preferably —NHR (R: a hydrogen atom, an alkyl group containing 1 to 6 carbon atoms), —OH, —SH, and —COOH, more preferably —OH; R represents a substituent selected from the group consisting of an alkyl group, a substituted alkyl group, a cycloalkyl group, an alkenyl group, an aralkyl group, an aryl group, a hydroxy group, an alkoxy group, a substituted alkoxy group, an amino group, a substituted amino group, an acylamino group, a sulfonylamino group, an acyl group, a nitro group, a cyano group, a halogen atom, an aryloxy group, a carbamoyl group, a substituted carbamoyl group, a sulfamoyl group, and a substituted sulfamoyl group; and n represents an integer of 0 to 4.

When heated, the base precursors of the present invention undergo a Lossen rearrangement and a base is released. Taking salicylhydroxamic acid carbamate, for instance, the decomposition reaction is shown by the following schematic:

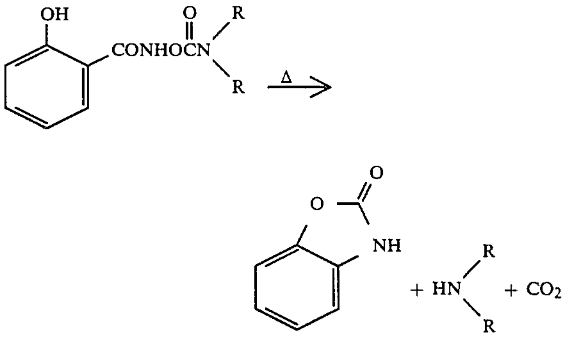

Losses rearrangement of hydroxamic acid derivatives generally gives isocyanates as products but, where amines are concurrently produced, the two react with each other to produce urea derivatives. Therefore, production of the urea derivative must be depressed to obtain base precursors which can be practically used.

A characteristic feature of the base precursor of the present invention is the presence of a nucleophilic group in the β-position with respect to the carbonyl group of the hydroxamic acid. This nucleophilic group functions for the isocyanate group produced by the Lossen rearrangement so that an intermolecular nucleophilic attack takes place rapidly with reactivity being lost, thus the produced amine effectively functioning as a base.

The base precursor of the present invention does not undergo a reverse reaction in spite of the presence of the amine near the reaction system. Hence they are effective for thermally developable photographic light-sensitive materials which are to be developed by heating in the absence of a water solvent.

Specific preferred examples of base precursors of the present invention are illustrated below.

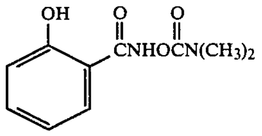

(1)

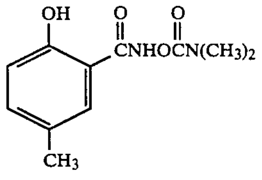

(2)

-continued
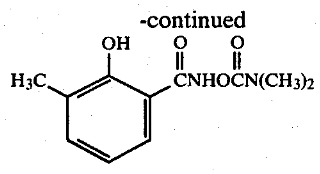
(3)
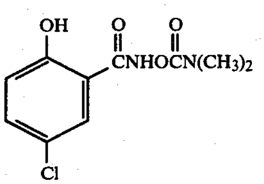
(4)
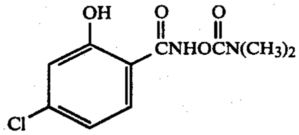
(5)
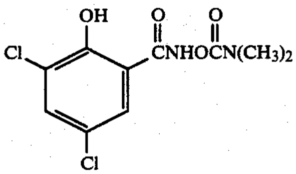
(6)
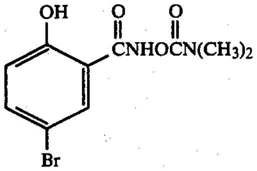
(7)
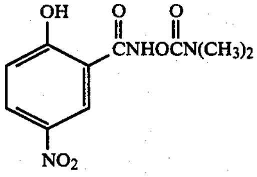
(8)
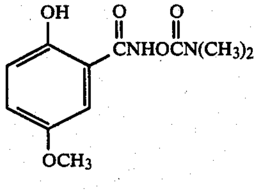
(9)
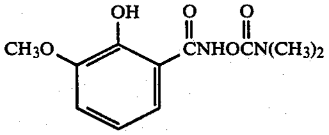
(10)
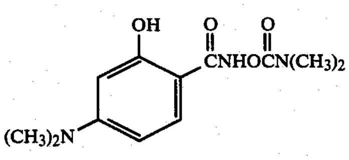
(11)
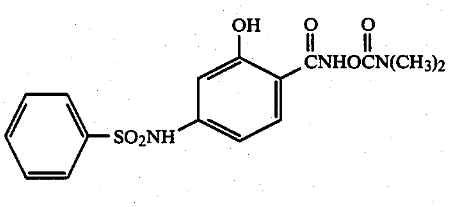
(12)
-continued
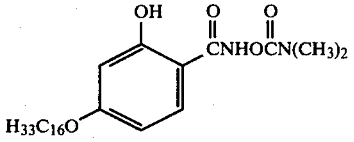
(13)
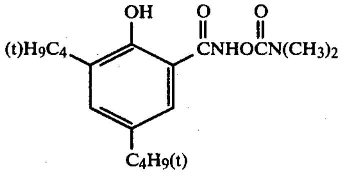
(14)
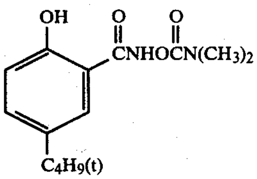
(15)
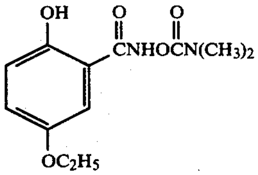
(16)
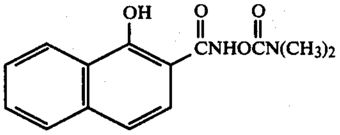
(17)
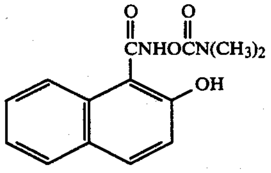
(18)
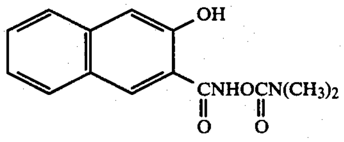
(19)
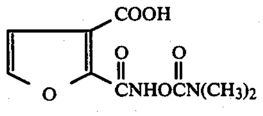
(20)
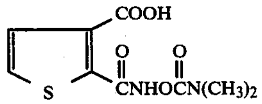
(21)
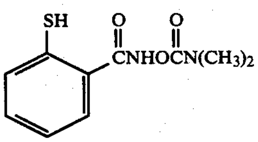
(22)

-continued
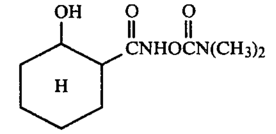
(23)
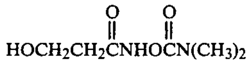
(24)
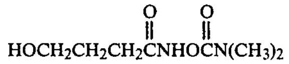
(25)
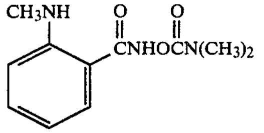
(26)
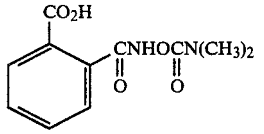
(27)
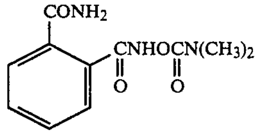
(28)
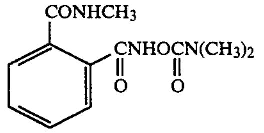
(29)
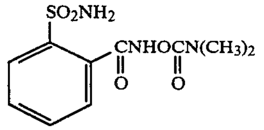
(30)
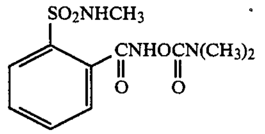
(31)
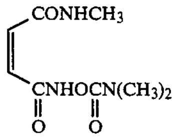
(32)
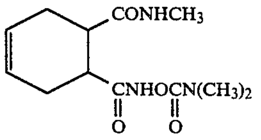
(33)
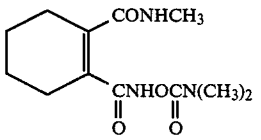
(34)
-continued
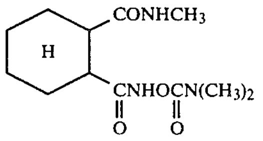
(35)
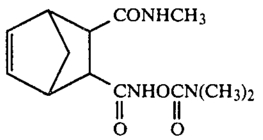
(36)
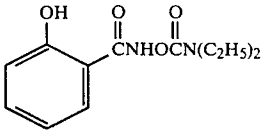
(37)
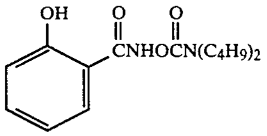
(38)
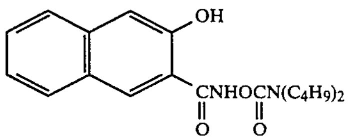
(39)
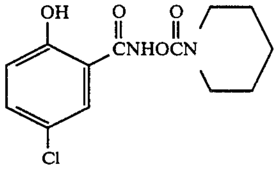
(40)
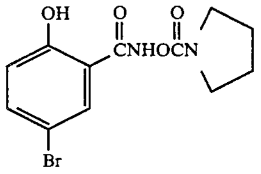
(41)
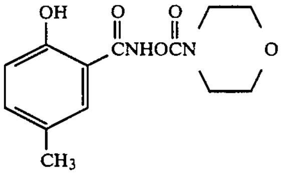
(42)
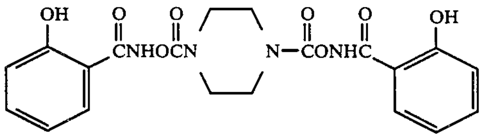
(43)
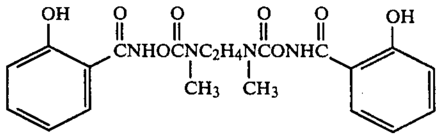
(44)

-continued

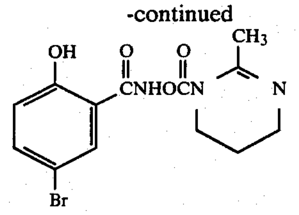

(45)

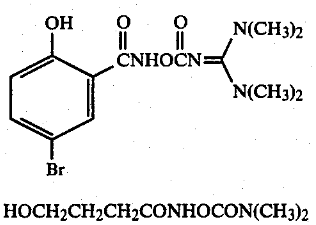

(46)

$HOCH_2CH_2CH_2CONHOCON(CH_3)_2$ (47)

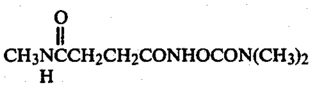

(48)

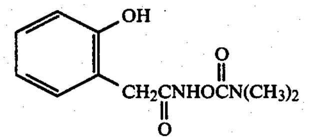

(49)

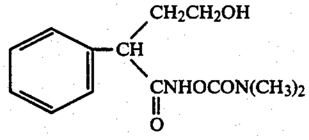

(50)

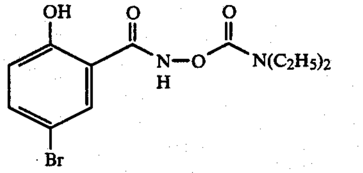

(51)

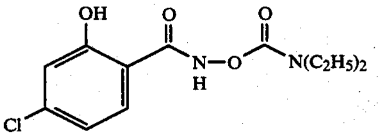

(52)

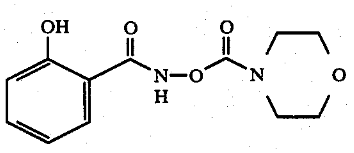

(53)

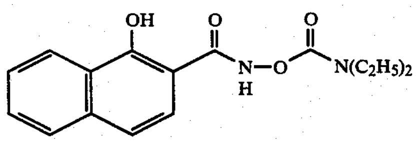

(54)

The compounds of the present invention shown above are illustrative and the invention should not be construed as being limited to the above-illustrated compounds.

Examples of the synthesis of base precursors of the present invention are described below.

The general synthesis process is as follows:

A carboxylic acid having a nucleophilic group, X, in the $\beta$-position is used as a starting material and, after esterification in a conventional manner, the resulting ester is reacted with hydroxylamine to obtain a hydroxamic acid derivative. Then, the sodium salt thereof is reacted with carbamyl chloride derivative in an aprotic polar solvent such as acetonitrile, tetrahydrofuran, etc., or the hydroxamic acid derivative is condensed with carbamyl chloride derivative in the presence of a suitable base such as triethylamine, pyridine, etc., to obtain the intended carbamate in high yield.

Where the nucleophilic group, X, can react with an ester group, a hydroxamic acid group or with carbamyl chloride during the esterification, hydroxamation or the final carbamation, which would lead to reduction in the yield of the desired end product, previous protection of X using a protective group removable under mild conditions, such as a trimethylsilyl group, a methoxyethoxymethyl group, a benzyl group or the like, and an appropriate removal of the protective group after the reactions provides the ability to obtain the end product in good yield.

Specific synthesis examples are described below. In the examples given hereafter unless otherwise indicated, all parts, percents, ratios and the like are by weight.

SYNTHESIS EXAMPLE 1

Salicylhydroxamic Acid, N,N-Dimethylcarbamate (1)

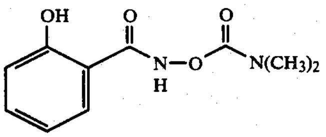

14 ml of triethylamine was gradually added to a dimethylformamide solution containing 15.3 g of salicylhydroxamic acid and 10 ml of N,N-dimethylcarbamyl fluoride, followed by stirring for ten hours. The reaction solution was poured into a weakly acidic ice-water to collect the precipitate by filtration, followed by drying. Yield: 18 g; mp. 95°–98° C. (dec.)

SYNTHESIS EXAMPLE 2

5-Bromosalicylhydroxamic Acid N,N-Dimethylcarbamate (7)

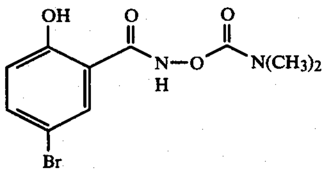

(2-1) Preparation of Phenyl 5-Bromosalicylate 80 ml of thionyl chloride was gradually added to a benzene suspension of 217 g of 5-bromosalicyclic acid and 113 g of phenol, followed by refluxing for ten hours under heating. After distilling off the benzene, ice-water was added to the residue, and the precipitate formed was collected by filtration, followed by drying. Yield: 210 g.

(2-2) Preparation of 5-Bromosalicylhydroxamic Acid

A methanol solution of 127 g of KOH was gradually added to a methanol solution of 210 g of phenyl 5-bromosalicylate prepared as in (2-1) above and 105 g of hydroxylamine hydrochloride. After stirring for 4 hours, the precipitate formed was collected by filtration. The precipitation was then suspended in water, and 60 ml of conc. hydrochloric acid (35%) was added thereto, followed by stirring for two hours to collect the precipitate by filtration followed by drying. Yield: 136 g.

(2-3) Preparation of 5-Bromosalicylhydroxamic Acid N,N-Dimethylcarbamate (7)

81 ml of triethylamine was gradually added to a dimethylformamide solution containing 136 g of 5-bromosalicylhydroxamic acid prepared as in (2-2) above and 54 ml of N,N-dimethylcarbamyl chloride at room temperature (about 20°-30° C.), then stirred for 10 hours. This solution was poured into ice-water to collect the precipitate by filtration followed by drying. Yield: 102 g; mp. 118°-119° C. (dec.)

SYNTHESIS EXAMPLE 3

Salicylhydroxamic Acid N,N-Dimethylcarbamate (38)

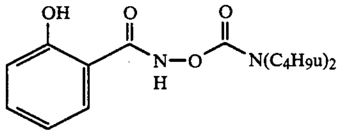

(3-1) Preparation of N,N-Dimethylcarbamyl Chloride 20 g of phosgene was absorbed by dichloromethane cooled to −40° C., and 8.4 g of dibutylamine was gradually added thereto. Excess phosgene and dichloromethane were distilled off at room temperature under reduced pressure. The residue was extracted with hexane, washed with water, and dried. Then, hexane was distilled off to obtain a colorless liquid. Yield: 7.5 g.

(3-2) Preparation of Salicylhydroxamic Acid N,N-Dibutylcarbamate (38)

6.0 g of salicylhydroxamic acid, 7.5 g of N,N-dimethylcarbamyl chloride prepared as in (3-1) above and 5.4 ml of triethylamine were reacted in the same manner as in Synthesis Example 1. The reaction solution was poured into ice-water, extracted with ethyl acetate, dried, and purified through column chromatography. Yield: 11.2 g (oil)

Other compounds of this invention than the above-described compounds of this invention can be synthesized according to the above-described process.

The base precursors of the present invention can be used in various fields.

One example thereof is to use them in thermally developable diazo copying materials, e.g., described in Japanese Patent Application (OPI) Nos. 11229/75, 109924/77, 45094/82, 133033/80 and 150014/77, Japanese Pat. Publication Nos. 19620/81, 24726/68, 40455/76, 41202/73 and 28663/69, etc.

In using the compounds in thermally developable diazo copying materials, a light-sensitive diazo compound, a coupling component, and a substance capable of producing a base upon heating, i.e., a base precursor, are incorporated in a light-sensitive layer. These copying materials undergo a coupling reaction when heated to about 100° to about 200° C. to form azo dyes.

The compounds of the present invention can be employed in the thermally developable diazo copying materials and the diazo copying process as described above.

Descriptions of thermally developable light-sensitive materials using silver halide and process of using them are found in, for example, Shashin Kogaku no Kiso (1979, Corona Co.), pp. 553-555, Eizo Joho (Apr. 1978), p. 40, *Nebletts Handbook of Photography and Reprography,* 7th ed. (Van Nostrand Reinhold Company), pp. 32-33, U.S. Pat. Nos. 3,152,904, 3,301,678, 3,392,020, 3,457,075, 3,531,286, 3,761,270, 3,985,565, 4,021,240, 4,022,617 and 4,235,957, British Pat. Nos. 1,131,108 and 1,167,777, Belgian Pat. No. 802,519, *Research Disclosure,* May, 1978, pp. 54-58 (RD-16966), ibid., June, 1978, pp. 9-15 (RD-17029), ibid., April, 1976, pp. 30-32 (RD-14453), ibid., December, 1976, pp. 14-15 (RD-15227), etc.

In the thermally developing process using silver halide, a light-sensitive material is used which comprises a support having thereon a layer containing (1) a light-sensitive silver halide emulsion, (2) a composition capable of producing a base upon heating, and (3) a developing agent for silver halide. When such a light-sensitive material is imagewise exposed and heated, the developing agent becomes activated with the base and exposed silver halide is reduced to form a silver image.

The compounds of the present invention can be employed in the silver halide type thermally developable light-sensitive materials as described above and the process using them.

Further, the compounds of the present invention can be employed in heat-sensitive materials as described in Japanese Pat. Publication No. 29024/76, Japanese Patent Application (OPI) Nos. 147949/75, 82421/78 and 99951/78, etc.

The base precursors of the present invention effectively produce bases in the substantial absence of water. Therefore, the base precursor of the present invention can be advantageously used in where chemical change is intended by a base to be produced by heating.

The amounts of the base precursors which can be used in the above-described cases will vary depending upon kind of compound and kind of system in which the compound is used. However, in general compound of the present invention is suitably used in an amount of 0.01 to 50 wt% based on the total weight of the coated layer, with 0.01 to 30 wt% being more preferable. The base precursors of the present invention may be used alone, or two or more of them may be used in combination, if desired. Further, they may be used together with base precursors outside the scope of the present invention.

The present invention is described in greater detail by the following examples which, however, are not to be construed as limiting the present invention in any way. Again, unless otherwise indicated, all parts percents, ratios and the like are by weight.

EXAMPLE 1

Test on Activity of Base Precursor 20 mg each of Base Precursors Nos. 1, 3, 4, 10 and 15 of the present invention was placed in test tubes and immersed in an oil bath heated to 150° C. After being allowed to cool, 1 ml of 50% ethanol was added thereto, and several drops of the following pH indicators were added thereto to observe what change of color occurred.

| pH Indicator | Color Change |
|---|---|
| A. Thymolphthalein ethanol solution (0.1%) | colorless→blue |
| B. 0.1% Ethanol solution of phenolphthalein | colorless→violet-red |
| C. 0.1% Ethanol solution of α-naptholphthalein | colorless→blue |

As a control, 20 mg of each of the above-described base precursors was dissolved in 1 ml of ethanol and, after adding thereto 1 ml of 50% ethanol, the pH indicators were added thereto to determine what color change occurred. As a result, every base precursor of the present invention described above was decomposed by heating to change the colors of all pH indicators A, B, and C as described above. In the control test, the colors of the pH indicators were not changed.

Additionally, the activity of the base precursor can be presented in the following order depending on the kind of pH indicators of which colors they can change.

| Activity | pH Indicators Changed in Color |
|---|---|
| large | A + B + C |
| ↕ | B + C |
| small | C alone |

From the above results, the base precursors of the present inventions are found to effectively produce bases upon being heated.

EXAMPLE 2

Measurement of Decomposition Rate of Base Precursor

About 400 mg of the base precursor of the present invention was dissolved in 25 ml of methanol. Separately, 400 mg of gelatin was dissolved in 5 ml of water with heating. After cooling, 5 ml of the above-described methanol solution was added thereto and the mixture well mixed. The resulting mixture solution was uniformly coated on a triacetyl cellulose support and dried to prepare samples.

The absorbance of each of the samples at λ max (around 300 nm) was previously measured, then the sample was heated on a hot plate at a definite temperature. The change in absorbance versus time was plotted to calculate first-order reaction rate.

Several examples of the reaction rate constants measured by the above-described method are given below.

| Sample | K at 140° C. ($\times 10^2$) | Half-Life Period $t_{\frac{1}{2}}$ (sec) |
|---|---|---|
| Base Precursor No. (1) | 6.7 | 10.3 |
| Base Precursor No. (37) | 3.7 | 18.7 |
| Base Precursor No. (38) | 9.0 | 7.7 |

In view of the fact that the half-life period of a known base precursor is 60 seconds, the above-described half-life periods reveal that the base precursors of the present invention have remarkably high activity.

EXAMPLE 3

Application to Thermally Developable Diazo Copying Material

A thermally developable diazo composition of the following formulation was coated on a polyethylene terephthalate support in a wet thickness of 100μ.

| | | |
|---|---|---|
| (a) | 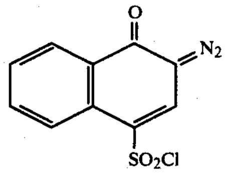 | 30 mg |
| (b) | 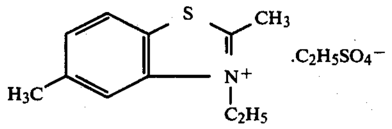 | 60 mg |
| (c) | Base Precursor (1) of the Present Invention | 120 mg |
| (d) | 10% Methylene Chloride Solution of Polyvinylidene Chloride | 5 ml |
| (e) | Acetone | 5 ml |

After drying, the sample was exposed to UV light through a transparent image original using a conventional diazo exposure apparatus, then uniformly heated on a heat block heated to 140° C. for 30 seconds to develop. A positive image having an optical density of 1.10 was obtained.

EXAMPLE 4

Application to Thermally Developable Silver Halide Light-Sensitive Material

A composition of the following formulation was uniformly coated in a wet thickness of 60μ on a polyethylene terephthalate support and dried to prepare a light-sensitive material.

| | |
|---|---|
| (a) Silver Bromoiodide Emulsion (AgI: 10 mol %; containing 5 wt % gelatin and silver) | 10 g |
| (b) Gelatin (10% aqueous solution) | 5 g |
| (c) Solution of 0.2 g of 2,6-Dichloro-p-aminophenol in 15 cc of Water | |
| (d) Coupler Dispersion (*) | 3.5 g |
| (e) Solution of 0.25 g of Base Precursor (1) of the Present Invention in 2.5 cc of Ethanol | |

The coupler dispersion (*) was prepared as follows.

5 g of 2-dodecylcarbamoyl-1-naphthol, 0.5 g of sodium 2-ethylhexyl succinate sulfonate, and 2.5 g of tricresyl phosphate (TCP) were weighed, and 30 ml of ethyl acetate was added thereto to dissolve these materials. This solution was mixed with 100 g of a 10% gelatin aqueous solution and stirred for dispersion.

The thus obtained light-sensitive material was imagewise exposed for 5 seconds at 2,000 lux using a tungsten electric lamp. When the material was uniformly heated on a heat block heated to 140° C. for 20 seconds, a negative cyan color image was obtained. The density of the image was measured using a Macbeth transmission densitometer (TD-504) to obtain a maximum density of 2.15.

While the invention has been described in detail and with reference to specific embodiments thereof, it will be apparent to one skilled in the art that various changes and modifications can be made therein without departing from the spirit and scope thereof.

What is claimed is:

1. A compound represented by the following formula (A-1) or (A-2):

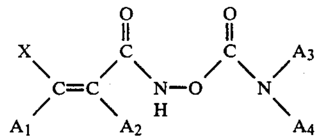

(A-1)

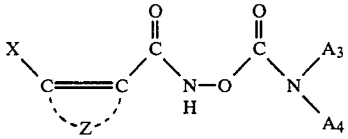

(A-2)

wherein $A_1$ and $A_2$ each represents a hydrogen atom, an alkyl group, a substituted alkyl group, a cycloalkyl group, an alkenyl group, an aralkyl group, an aryl group, a substituted aryl group, an acyl group, or a heterocyclic group, $A_3$ and $A_4$ each represents a hydrogen atom, an alkyl group, a substituted alkyl group, a cycloalkyl group, or an aralkyl group, and $A_3$ and $A_4$ can combine to form a ring or the group

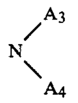

represents an imino group selected from the group

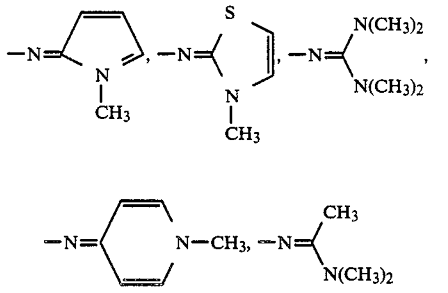

and X represents a nucleophilic group, and

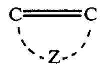

is a 5 or 6 member aromatic ring or a 5 or 6 membered heterocyclic group containing an oxygen atom, a sulfur atom or a nitrogen atom, wherein said substituted alkyl groups for $A_1$, $A_2$, $A_3$ and $A_4$ are substituted with one or more of a hydroxy group, an alkoxy group, a cyano group, a carboxyl group, a carboalkoxy group, a carbamoyl group or a halogen atom as a substituent and said substituted aryl group is substituted with one or more of an alkyl goup, an alkoxy group, a dialkylamino group, a cyano group, a nitro group, or a halogen atom as a substituent.

2. The compound of claim 1, wherein said alkyl group is a straight or branched chain alkyl group containing 1 to 18 carbon atoms, said cycloalkyl group is a 5- to 6-membered cycloalkyl group containing 5to 10 carbon atoms, said alkenyl group contains 2 to 10 carbon atoms, said aralkyl group contains 7 to 10 carbon atoms, said aryl group is a monocyclic or bicyclic group containing 5 to 15 carbon atoms, said heterocyclic group is 5 to 7 membered group containing one or more of a N atom, a S atom and a O atom as hetero atoms, and said acyl group is an acyl group containing 2 to 18 carbon atoms.

3. The compound of claim 1, wherein said nucleophilic group for X is a hydroxy group, a hydroxymethyl group, an amino group, an aminomethyl group, a mercapto group, a mercaptomethyl group, a carboxyl group, a carbamoyl group, or a sulfamoyl group.

4. The compound of claim 1, wherein said base precursor is represented by the following formula (C)

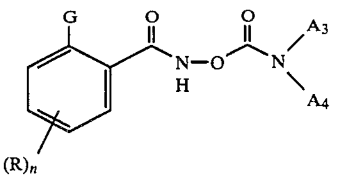

(C)

wherein G represents a nuclophilic group; R represents a substituent selected from the group consisting of an alkyl group, a cycloalkyl group, an alkenyl group, an aralkyl group, an aryl group, a hydroxy group, an alkoxy group, an amino group, an acylamino group, a sulfonylamino group, an acyl group, a nitro group, a cyano group, a halogen atom, an aryloxy group, a carbamoyl group, or a sulfamoyl group; and n represents an integer of 0 to 4.

5. A base precursor represented by the formula

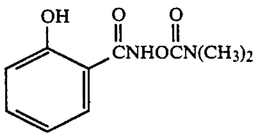

(1)

* * * * *